(12) United States Patent
Ibi et al.

(10) Patent No.: US 9,822,062 B2
(45) Date of Patent: Nov. 21, 2017

(54) METHOD AND APPARATUS FOR PRODUCING DICYANOBENZENE

(71) Applicant: MITSUBISHI GAS CHEMICAL COMPANY, INC., Chiyoda-ku (JP)

(72) Inventors: Yukiya Ibi, Kurashiki (JP); Tatsuyuki Kumano, Kurashiki (JP); Natsumi Wakita, Kurashiki (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 41 days.

(21) Appl. No.: 15/025,812

(22) PCT Filed: Mar. 9, 2015

(86) PCT No.: PCT/JP2015/056776
§ 371 (c)(1),
(2) Date: Mar. 29, 2016

(87) PCT Pub. No.: WO2015/137267
PCT Pub. Date: Sep. 17, 2015

(65) Prior Publication Data
US 2017/0217873 A1    Aug. 3, 2017

(30) Foreign Application Priority Data

Mar. 10, 2014 (JP) .................................. 2014-046426

(51) Int. Cl.
| | | |
|---|---|---|
| C07C 209/48 | (2006.01) | |
| C07C 211/00 | (2006.01) | |
| C07C 253/34 | (2006.01) | |
| C07C 253/28 | (2006.01) | |
| B01D 53/14 | (2006.01) | |
| B01D 11/04 | (2006.01) | |
| B01D 17/02 | (2006.01) | |
| B01D 19/00 | (2006.01) | |
| B01D 1/00 | (2006.01) | |
| B01D 3/14 | (2006.01) | |

(52) U.S. Cl.
CPC .......... *C07C 209/48* (2013.01); *B01D 1/0082* (2013.01); *B01D 3/14* (2013.01); *B01D 11/0492* (2013.01); *B01D 17/0214* (2013.01); *B01D 19/00* (2013.01); *B01D 53/1418* (2013.01); *B01D 53/1493* (2013.01); *C07C 253/28* (2013.01); *C07C 253/34* (2013.01); *B01D 2252/2053* (2013.01)

(58) Field of Classification Search
None
See application file for complete search history.

(56) References Cited

U.S. PATENT DOCUMENTS

| | | | |
|---|---|---|---|
| 4,985,581 | A | 1/1991 | Saito et al. |
| 2013/0296609 | A1 | 11/2013 | Kumano et al. |

FOREIGN PATENT DOCUMENTS

| | | | |
|---|---|---|---|
| CN | 103339098 | A | 10/2013 |
| EP | 1 157 969 | A2 | 11/2001 |
| JP | 42-10856 | B | 6/1967 |
| JP | 1-275551 | A | 11/1989 |
| JP | 5-170724 | A | 7/1993 |
| JP | 9-71561 | A | 3/1997 |
| JP | 11-246506 | A | 9/1999 |
| JP | 2003-267942 | A | 9/2003 |
| WO | WO 2012/105498 | A1 | 8/2012 |

OTHER PUBLICATIONS

International Search Report dated May 26, 2015, in PCT/JP2015/056776 filed Mar. 9, 2015.

*Primary Examiner* — Kristin Vajda
(74) *Attorney, Agent, or Firm* — Oblon, McClelland, Maier & Neustadt, L.L.P.

(57) ABSTRACT

The object is to prevent deterioration and loss of dicyanobenzene in producing dicyanobenzene by ammoxidation of xylene to thereby achieve industrial and economical advantage in producing of dicyanobenzene. The method for producing dicyanobenzene of the present invention includes: contacting a xylene-ammoxidation reaction gas containing dicyanobenzene in ammoxidation of xylene with an organic solvent so as to obtain a dicyanobenzene-absorbing solution; contacting the dicyanobenzene-absorbing solution with a basic aqueous solution containing a salt such as ammonium carbonate so as to extract a water-soluble salt formed by neutralization reaction between carboxylic acid in the dicyanobenzene-absorbing solution and a base in the basic aqueous solution into an aqueous phase; separating the mixture of the dicyanobenzene-absorbing solution and the basic aqueous solution into an organic phase and an aqueous phase; decomposing the salt such as ammonium carbonate contained in the organic phase for separation of the salt from the organic phase; and distilling the organic phase to separate low boiling point compounds contained in the organic phase from the organic phase so as to obtain dicyanobenzene.

20 Claims, 1 Drawing Sheet

METHOD AND APPARATUS FOR PRODUCING DICYANOBENZENE

TECHNICAL FIELD

The present invention relates to a method for producing dicyanobenzene by ammoxidation of xylene, and a producing apparatus for use in the producing method.

BACKGROUND ART

Dicyanobenzene is a useful compound as a raw material of agricultural chemicals and an intermediate raw material of polyamide resins and curing agents. Dicyanobenzene can be produced by a known method involving ammoxidizing xylene (ortho-xylene, meta-xylene and para-xylene), for example, any method described in Patent Documents 1 to 5. Further, the produced dicyanobenzene may be hydrogenated by a known hydrogenation reaction so as to produce xylylenediamine, which is useful in various industrial fields such as resin curing agents, nylon, polyurethane, rubber chemicals, paper processing chemicals, and fiber treatment agents.

In hydrogenation of dicyanobenzene to produce xylylenediamine with use of a hydrogenation catalyst, it is known that use of dicyanobenzene obtained by a specific method extends the life of a hydrogenation catalyst (refer to Patent Document 6). In the specific method, first, the reaction gas in ammoxidation of xylene is contacted with an organic solvent so as to obtain a dicyanobenzene-absorbing solution comprising the organic solvent in which dicyanobenzene is dissolved. Subsequently, the dicyanobenzene-absorbing solution is contacted with a basic aqueous solution so as to cause liquid-liquid separation into an organic phase and an aqueous phase, and the aqueous phase is then removed. The organic phase is then distilled to separate compounds having a boiling point lower than that of dicyanobenzene from the organic phase, so that dicyanobenzene is obtained.

CITATION LIST

Patent Document

Patent Document 1: Japanese Patent Application Laid-Open No. 1-275551
Patent Document 2: Japanese Patent Application Laid-Open No. 5-170724
Patent Document 3: Japanese Patent Application Laid-Open No. 9-71561
Patent Document 4: Japanese Patent Application Laid-Open No. 11-246506
Patent Document 5: Japanese Patent Application Laid-Open No. 2003-267942
Patent Document 6: International Publication No. WO 2012/105498

SUMMARY OF INVENTION

Technical Problem

The dicyanobenzene obtained by the method described in Patent Document 6 hardly causes deterioration in activity of heterogeneous metal catalysts due to little content of carboxylic acids. Accordingly, the dicyanobenzene obtained by the method can be a useful raw material of various derivatives including xylylenediamine, of which the synthesis requires the heterogeneous metal catalysts.

However, obtaining such dicyanobenzene under industrial conditions using a basic aqueous solution containing one or more salts selected from the group consisting of ammonium carbonate, ammonium bicarbonate and ammonium carbamate has the following problem. Namely, a non-ignorable amount of the salt originally contained in the basic aqueous solution is dissolved in the organic phase after liquid-liquid separation. The dissolved salt accelerates the formation of cyanobenzamide from dicyanobenzene and water in a step after liquid-liquid separation. Consequently dicyanobenzene is lost.

In view of the circumstances, it is an object of the present invention to provide a method and apparatus for producing dicyanobenzene by ammoxidation of xylene, capable of preventing deterioration and loss of dicyanobenzene so as to achieve industrial and economical advantage in producing of dicyanobenzene.

Solution to Problem

As a result of intensive studies to achieve the above object, the present inventors have found that, in a producing method with use of a basic aqueous solution containing one or more salts selected from the group consisting of ammonium carbonate, ammonium bicarbonate and ammonium carbamate, the problem can be solved by incorporating a step of decomposing the salt contained in an organic phase after a prescribed step into gas for separation, together with other various steps.

In other words, the present invention is as follows.

[1] A method for producing dicyanobenzene comprising: (1) an absorption step of contacting a xylene-ammoxidation reaction gas containing dicyanobenzene obtained by ammoxidation of xylene with an organic solvent so as to obtain a dicyanobenzene-absorbing solution containing the organic solvent in which the dicyanobenzene is dissolved; (2) an extraction step of contacting the dicyanobenzene-absorbing solution with a basic aqueous solution containing one or more salts selected from the group consisting of ammonium carbonate, ammonium bicarbonate, and ammonium carbamate so as to extract a water-soluble salt formed by neutralization reaction between carboxylic acid in the dicyanobenzene-absorbing solution and a base in the basic aqueous solution into an aqueous phase; (3) a liquid-liquid separation step of separating a mixture of the dicyanobenzene-absorbing solution and the basic aqueous solution after the extraction step into an organic phase and an aqueous phase; (4) a degassing step of decomposing one or more salts selected from the group consisting of ammonium carbonate, ammonium bicarbonate, and ammonium carbamate contained in the organic phase after the liquid-liquid separation step so as to separate the one or more salts from the organic phase; and (5) a low-boiling-point compound separation step of distilling the organic phase after the degassing step to separate components contained in the organic phase and having a boiling point lower than that of the dicyanobenzene, from the organic phase so as to obtain the dicyanobenzene.

[2] The method according to [1], wherein a pressure of a gas phase in the degassing step is 101.3 kPa or less.
[3] The method according to [1] or [2], wherein a temperature of a liquid phase in the degassing step is 70 to 180° C.
[4] The method according to any one of [1] to [3], wherein the base in the extraction step is ammonia in an amount in a number of moles 1 to 50 times the total number of moles of the carboxylic acid contained in the dicyanobenzene-absorbing solution.

[5] The method according to any one of [1] to [4], wherein the basic aqueous solution is contacted with the dicyanobenzene-absorbing solution under a temperature condition of 140° C. or lower in the extraction step.

[6] The method according to any one of [1] to [5], wherein the xylene is meta-xylene and the dicyanobenzene is isophthalonitrile.

[7] The method according to any one of [1] to [6], wherein a catalyst for use in the ammoxidation reaction is a catalyst which contains vanadium and/or chromium.

[8] The method according to any one of [1] to [7], wherein the organic solvent which absorbs the dicyanobenzene in the absorption step is one or more organic solvents selected from the group consisting of an alkylbenzene, a heterocyclic compound, an aromatic nitrile compound and a heterocyclic nitrile compound.

[9] A method for producing xylylenediamine from the dicyanobenzene obtained by the producing method according to any one of [1] to [8], comprising a hydrogenation step of dissolving the dicyanobenzene in a solvent and subsequently hydrogenating the dicyanobenzene in a liquid phase in the presence of a catalyst.

[10] An apparatus for producing dicyanobenzene comprising: (1) absorption means for contacting a xylene-ammoxidation reaction gas containing dicyanobenzene obtained by ammoxidation of xylene with an organic solvent so as to obtain a dicyanobenzene-absorbing solution containing the organic solvent in which the dicyanobenzene is dissolved; (2) extraction means for contacting the dicyanobenzene-absorbing solution with a basic aqueous solution containing one or more salts selected from the group consisting of ammonium carbonate, ammonium bicarbonate, and ammonium carbamate so as to extract a water-soluble salt formed by neutralization reaction between carboxylic acid in the dicyanobenzene-absorbing solution and a base in the basic aqueous solution into an aqueous phase; (3) liquid-liquid separation means for separating a mixture of the dicyanobenzene-absorbing solution and the basic aqueous solution sent from the extraction means into an organic phase and an aqueous phase; (4) degassing means for decomposing one or more salts selected from the group consisting of ammonium carbonate, ammonium bicarbonate, and ammonium carbamate contained in the organic phase sent from the liquid-liquid separation means, so as to separate the one or more salts from the organic phase; and (5) low-boiling-point compound separation means for distilling the organic phase sent from the degassing means to separate components contained in the organic phase and having a boiling point lower than that of the dicyanobenzene, from the organic phase so as to obtain the dicyanobenzene.

Advantageous Effect of Invention

According to the present invention, a method and apparatus for producing dicyanobenzene by ammoxidation of xylene can be provided which are capable of preventing deterioration and loss of dicyanobenzene so as to achieve industrial and economical advantage in producing of dicyanobenzene.

DESCRIPTION OF EMBODIMENT

The embodiment of the present invention (hereinafter referred to simply as "present embodiment") will be described in detail as follows with reference to the drawing as needed, but the present invention is not limited to the present embodiment. Various modifications may be made on the present invention without departing from the spirit of the invention. In the drawing, the same symbol is assigned to the same element, and redundant description is omitted. The positional relationships such as top and bottom or right and left are based on the relationships illustrated in the drawing, unless otherwise specified. Further, the dimensional proportions in the drawing are not limited to the illustrated proportions.

(Method for Producing Dicyanobenzene)

The method for producing dicyanobenzene of the present embodiment includes: (1) an absorption step of contacting a xylene-ammoxidation reaction gas containing dicyanobenzene obtained by ammoxidation of xylene with an organic solvent so as to obtain a dicyanobenzene-absorbing solution containing the organic solvent in which the dicyanobenzene is dissolved; (2) an extraction step of contacting the dicyanobenzene-absorbing solution with a basic aqueous solution containing one or more salts selected from the group consisting of ammonium carbonate, ammonium bicarbonate, and ammonium carbamate so as to extract a water-soluble salt formed by neutralization reaction between carboxylic acid in the dicyanobenzene-absorbing solution and a base in the basic aqueous solution into an aqueous phase; (3) a liquid-liquid separation step of separating a mixture of the dicyanobenzene-absorbing solution and the basic aqueous solution after the extraction step into an organic phase and an aqueous phase; (4) a degassing step of decomposing one or more salts selected from the group consisting of ammonium carbonate, ammonium bicarbonate and ammonium carbamate contained in the organic phase after the liquid-liquid separation step so as to separate the one or more salts from the organic phase; and (5) a low-boiling-point compound separation step of distilling the organic phase after the degassing step to separate the components contained in the organic phase and having a boiling point lower than that of the dicyanobenzene, from the organic phase, so as to obtain the dicyanobenzene.

In the present invention, "dicyanobenzene" means phthalonitrile (i.e. 1,2-dicyanobenzene), isophthalonitrile (i.e. 1,3-dicyanobenzene), or terephthalonitrile (i.e. 1,4-dicyanobenzene), which can be produced from each of the corresponding xylenes, i.e. ortho-xylene, meta-xylene or para-xylene by a known ammoxidizing method.

(1) Absorption Step

In the absorption step, the xylene-ammoxidation reaction gas containing dicyanobenzene obtained by ammoxidation of xylene is contacted with an organic solvent, so that dicyanobenzene is absorbed in the organic solvent.

The ammoxidation reaction may be performed by a known method. For example, a reaction raw material gas including the mixture of xylene, oxygen and ammonia may be contacted with a catalyst for the ammoxidation reaction so as to perform the ammoxidation reaction under conditions described below. The type of a catalyst bed in the ammoxidation reaction may be either of a fluidized bed and a fixed bed. As a catalyst for use in the ammoxidation reaction, known catalysts, for example, such as those described in Patent Document 1, 2, 4 or 5, may be used. Among them, a catalyst including vanadium and/or chromium is more preferred. The amount of ammonia fed for use in the ammoxidation reaction is preferably in the range of 2 to 20 mol, more preferably 6 to 15 mol, based on 1 mol of xylene. With the amount of ammonia fed within the range, the yield of dicyanobenzene is further improved and the space time yield is also further improved. The unreacted ammonia contained in the ammoxidation reaction gas including a mixture of a product gas of ammoxidation reaction and an unreacted reaction raw material gas may be collected for reuse in the ammoxidation reaction. The amount of oxygen fed for use in the ammoxidation reaction is preferably in the range of 3 mol or more, more preferably in the range of 3 to 100 mol, furthermore preferably in the range of 4 to 100 mol, based on 1 mol of xylene. With the amount of oxygen fed within the range, the yield of dicyanobenzene is further improved and the space time yield is also further improved. Air may be used as the supply source of oxygen.

The reaction temperature of the ammoxidation reaction is preferably in the rage of 300 to 500° C., more preferably in the range of 330 to 470° C. With a reaction temperature within the range, the conversion of xylene is more improved, and the generation of carbon dioxide, hydrogen cyanide, and the like is suppressed, so that dicyanobenzene can be produced at a further improved yield. Though the ammoxidation reaction pressure may be any of the normal pressure, an increased pressure (i.e. a pressure higher than normal pressure) and a reduced pressure (i.e. a pressure lower than normal pressure), the range from normal pressure (atmospheric pressure: e.g. 100 kPa) to 300 kPa is preferred from the same viewpoint as that of the reaction temperature. Further, the reaction raw material in the ammoxidation reaction has a gas hourly space velocity (GHSV) of preferably 500 to 5000 $h^{-1}$.

In the absorption step, "absorbing dicyanobenzene into an organic solvent" means dissolving dicyanobenzene in an ammoxidation reaction gas into an organic solvent. An organic solvent having a boiling point lower than that of dicyanobenzene, a relatively high solubility of dicyanobenzene, and inertness to dicyanobenzene is preferred for use in absorbing dicyanobenzene. Examples of the organic solvent satisfying the conditions include: an alkylbenzene such as xylene (an ortho isomer, a meta isomer and a para isomer), pseudocumene, mesitylene and ethylbenzene; a heterocyclic compound such as methylpyridine; an aromatic nitrile compound such as tolunitrile (an ortho isomer, a meta isomer and a para isomer) and benzonitrile; and a heterocyclic nitrile compound such as cyanopyridine; and one or more organic solvents selected from the group consisting thereof is preferred. Among them, tolunitrile is particularly preferred from the viewpoint of utilization of byproduct in the ammoxidation reaction.

From the viewpoint of efficiently and reliably absorbing dicyanobenzene in the absorption step, the ammoxidation reaction gas is preferably contacted with an organic solvent at 80 to 200° C., or preferably contacted with an organic solvent for 1 to 30 seconds. The ammoxidation reaction gas is more preferably contacted with an organic solvent such that both of conditions are satisfied. The amount of the organic solvent used in the absorption step is preferably 0.5 to 20 parts by mass based on 1 part by mass of dicyanobenzene from the viewpoint of more efficient and reliable absorption of dicyanobenzene. In order to allow the organic solvent to be contacted with the ammoxidation reaction gas, a gas-liquid contacting apparatus or the like may be used. In the apparatus, the type of flows of the organic solvent and the ammoxidation reaction gas may be either of a counter-flow and a parallel-flow. Alternatively, a container for holding the organic solvent may have a gas injection inlet at the bottom, through which the ammoxidation reaction gas is fed into the organic solvent to achieve the contact between both.

(2) Extraction Step

In the extraction step, the dicyanobenzene-absorbing solution obtained in the absorption step is contacted with a basic aqueous solution so as to extract a water-soluble salt formed by neutralization reaction between a carboxylic acid in the dicyanobenzene-absorbing solution and a base in the basic aqueous solution into an aqueous phase. Herein, the carboxylic acid is a byproduct in the ammoxidation reaction, and examples thereof include cyanobenzoic acid (an ortho isomer, a meta isomer, and a para isomer), methylbenzoic acid (an ortho isomer, a meta isomer, and a para isomer), and phthalic acid (an ortho isomer, a meta isomer, and a para isomer).

In order to allow the dicyanobenzene-absorbing solution to be efficiently contacted with the basic aqueous solution, a mixing tank having an agitator may be used, or a tube-type mixer such as a static mixer may be used. Alternatively, jet mixing to merge the basic aqueous solution into the flow of the dicyanobenzene-absorbing solution may be employed without use of an apparatus for mixing. The type of extraction in the extraction step may be any of a batch process, a semi-batch process, and a continuous process.

The base contained in the basic aqueous solution is not particularly limited, and either of an inorganic base and an organic base may be used. Examples of the base include ammonia, sodium hydroxide, and potassium hydroxide. Among them, ammonia is preferred due to the necessity that the salt formed from the neutralization reaction with a carboxylic acid in the dicyanobenzene-absorbing solution is soluble in water, the availability at low cost, and the capability for more efficiently neutralizing the carboxylic acid in the dicyanobenzene-absorbing solution.

The amount of base (e.g. ammonia) used may be equal to or more than the total amount of carboxylic acid contained in the dicyanobenzene-absorbing solution on the molar basis. More specifically the amount of the base used is preferably a number of moles 1 to 50 times the total number of moles of the carboxylic acids contained in the dicyanobenzene-absorbing solution, more preferably 2 to 30 times, furthermore preferably 3 to 15 times. The concentration of ammonia in the basic aqueous solution may be properly adjusted depending on the amount of carboxylic acids contained in the dicyanobenzene-absorbing solution. More specifically, the concentration of ammonia in the basic aqueous solution is preferably 0.1 to 20% by mass, more preferably 0.1 to 10% by mass.

The amount of the basic aqueous solution used based on the amount of the dicyanobenzene-absorbing solution is industrially preferably equal to or less than the amount of the dicyanobenzene-absorbing solution on the mass bases, though not particularly limited. More specifically, the amount of an ammonia aqueous solution used as the basic aqueous solution is preferably 1 to 100% by mass, more preferably 2 to 50% by mass, furthermore preferably 5 to 30% by mass, based on the amount of the dicyanobenzene-absorbing solution. An aqueous phase to be collected in the subsequent liquid-liquid separation step may be used as a part of or as the whole of the basic aqueous solution. Preferably the basic aqueous solution contains one or more salts selected from the group consisting of ammonium carbonate, ammonium bicarbonate and ammonium carbamate in advance, considering the subsequent liquid-liquid separation operation. Due to the increased liquid density resulting from the salt dissolved in the basic aqueous solution so as to coexist with the base, the separation speed of the liquid-liquid separation can be accelerated without causing negative effects on the extraction of carboxylic acid. The salts may be used singly or in any combination. In particular, an aqueous solution in which ammonium carbonate and ammonia are dissolved can be easily prepared at low cost by passing a carbon dioxide-containing gas through an ammonia aqueous solution. Such an aqueous solution is therefore an industrially useful extracting agent, i.e. an industrially preferred basic aqueous solution. The amount of the salt used is properly adjusted depending on the separation speed required for the liquid-liquid separation step. The amount of the salt dissolved in the basic aqueous solution is typically 1 to 30% by mass based on the amount of the basic aqueous solution.

The temperature for the dicyanobenzene-absorbing solution to be contacted with the basic aqueous solution (hereinafter referred to as "contact temperature" in this step) is preferably 70° C. to 140° C., more preferably 70° C. to 120° C., furthermore preferably 70° C. to 110° C. With a contact temperature of 140° C. or lower, formation of a large amount of cyanobenzamide, cyanobenzoic acid and phthalamide from dicyanobenzene can be prevented, so that dicyanobenzene is prevented from dissolving into an aqueous phase. In other words, the loss of dicyanobenzene can be prevented, which is preferred. On the other hand, the lower limit of the contact temperature may be any temperature, as long as the dissolved state of dicyanobenzene can be maintained in the dicyanobenzene-absorbing solution. In the case of a solution of isophthalonitrile absorbed in meta-tolunitrile at an isophthalonitrile concentration of 10% by mass, for example, the contact temperature may be controlled at a liquid temperature of 70° C. or higher. Consequently the precipitation of isophthalonitrile can be prevented, which is preferred.

In order to reduce the amount of waste water, the aqueous phase to be collected in the subsequent liquid-liquid separation step may be used as a part of or as the whole of the basic aqueous solution. An organic solvent may be added to the aqueous phase to be collected so as to make an emulsion, and the emulsion may be contacted with the dicyanobenzene-absorbing solution. Examples of the organic solvent to be added in this case include an alkylbenzene such as xylene (an ortho isomer, a meta isomer and a para isomer), pseudocumene, mesitylene and ethylbenzene; a heterocyclic compound such as methylpyridine; an aromatic nitrile compound such as tolunitrile (an ortho isomer, a meta isomer, and a para isomer) and benzonitrile; and a heterocyclic nitrile compound such as cyanopyridine; and one or more organic solvents selected from the group consisting thereof is preferred from the viewpoint of the emulsion formation. Further, the organic solvent used in the absorption step is particularly preferably used in the preparation of the emulsion.

The pressure under which the dicyanobenzene-absorbing solution is contacted with the basic aqueous solution (hereinafter referred to as "contact pressure" in this step) is properly adjusted between atmospheric pressure and a pressurized state depending on temperature conditions. The contact pressure may be any pressure, as long as the dicyanobenzene-absorbing solution and at least a part of the basic aqueous solution keep the liquid phase with the base being present in the aqueous phase in an amount required for neutralization with carboxylic acids. An inert gas such as nitrogen gas and argon gas may coexist as necessary. With use of ammonium carbonate, ammonium bicarbonate and ammonium carbamate singly or in any combination as the salts contained in the basic aqueous solution, at a contact temperature of 140° C. or lower, the contact pressure may be properly adjusted in the range of 1.6 MPaG or less.

The time required for the dicyanobenzene-absorbing solution to be contacted with the basic aqueous solution is preferably 2 hours or less, more preferably 1 hour or less, furthermore preferably 30 minutes or less, from the viewpoint of reducing the loss of dicyanobenzene. A time of several seconds to 30 minutes is typically sufficient, though depending on a method for contacting dicyanobenzene-absorbing solution with the basic aqueous solution.

The water-soluble salts to be formed in the aqueous phase in the extraction step are the salts of carboxylic acids and the base, and examples thereof include ammonium cyanobenzoate, methyl ammonium benzoate, and ammonium phthalate.

(3) Liquid-Liquid Separation Step

In the liquid-liquid separation step, a mixture of the dicyanobenzene-absorbing solution and the basic aqueous solution after the extraction step is separated into an organic phase and an aqueous phase. In other words, an organic phase and an aqueous phase are phase-separated. The separation method may include keeping the mixture standing for phase separation. Other than the above, examples of the separation method include known methods such as use of a centrifugal separator and combination use of a coalescer and a separator. Although the temperature and pressure conditions for the liquid-liquid separation are not particularly limited as long as the phases can be separated, conditions similar to those of the extraction step are preferred. With a temperature and a pressure for the liquid-liquid separation substantially lowered from the temperature and the pressure in the extraction step, a small amount of dicyanobenzene dissolved in the aqueous phase is precipitated not only to cause clogging of piping but also to cause difficulty for the aqueous phase to keep the liquid phase state, resulting in difficulty in separation.

(4) Degassing Step

In the degassing step, one or more salts selected from ammonium carbonate, ammonium bicarbonate, and ammonium carbamate contained in an organic phase after the liquid-liquid separation step is decomposed to separate the salt from the organic phase. On this occasion, the salt is separated as gas.

The organic phase separated from the aqueous phase in the liquid-liquid separation step contains the basic aqueous solution used in the extraction step in an amount corresponding to the solubility thereof. Accordingly, the salt originally dissolved in the organic phase accelerates the formation of cyanobenzamide from dicyanobenzene and water, particularly in the range from completion of the liquid-liquid separation to the distillation treatment in the subsequent stage, resulting in the loss of dicyanobenzene. Consequently, the amount of loss of dicyanobenzene increases with the content of the salts in the organic phase. On the other hand, when the salts dissolved in the organic phase are separated from the organic phase together with components having a lower boiling point than that of dicyanobenzene (hereinafter also referred to as "low boiling point compounds"), the deterioration of dicyanobenzene is accelerated due to elevated temperature of the organic phase, so that the loss of dicyanobenzene is more easily caused. In contrast, in the present embodiment, the salts contained in the organic phase are reduced by decomposition and separation in the present degassing step, so that the loss of dicyanobenzene can be suppressed. In the following low-boiling-point compound separation step, low boiling point compounds may be separated from the organic phase after separation of the salts in the present step, so that the deterioration of dicyanobenzene can be suppressed than before, even with an elevated temperature of the organic phase. Further, the water content in the organic phase can be reduced in addition to the reduction of the salts in the organic phase in the present degassing step. The reduction of water as raw material of the reaction to form cyanobenzamide together with dicyanobenzene can further suppress the loss of dicyanobenzene.

When the organic phase is subjected to specific temperature and pressure conditions in the present step, the one or more salts selected from the group consisting of ammonium carbonate, ammonium bicarbonate and ammonium carbamate contained in an organic phase can be decomposed into carbon dioxide and ammonia, i.e. gases to be removed. On the other hand, preferably the pressure and temperature in the present step are set such that carbon dioxide and ammonia formed after decomposition of the salts accompany other gas components in the organic phase as little as possible. Specifically, the pressure of the gas phase (at the top of a column, when a degassing column is used in the present step) is preferably set such that the temperature is reached at which the content of carbonate ions and ammonium ions in the organic phase to be extracted are reduced to approximately the same content of the respective ions in the dicyanobenzene-absorbing solution in the absorption step. More specifically the pressure of the gas phase may be the atmospheric pressure (101.3 kPa) or under reduced pressure conditions (less than 101.3 kPa), preferably 101.3 kPa or less, more preferably 70 kPa or less, furthermore preferably 50 kPa or less. The pressure of the gas phase is preferably 10 kPa to 101.3 kPa, more preferably 10 kPa to 70 kPa, furthermore preferably 10 kPa to 50 kPa, from the viewpoints of further suppressing the loss of dicyanobenzene, more reliably decomposing and separating the salts, and keeping the dissolved state of dicyanobenzene in the organic phase so as to suppress the deterioration thereof.

From the same viewpoints as those for the pressure, the temperature of the liquid phase (at the bottom of a column, when a degassing column is used in the present step) is preferably 70 to 180° C., more preferably 90 to 160° C., furthermore preferably 100 to 140° C. In the case where the organic phase is a solution of isophthalonitrile absorbed in meta-tolunitrile at an isophthalonitrile concentration of 10% by mass, for example, the temperature of the liquid phase is preferably 70° C. or higher.

With a pressure and a temperature under the above-mentioned conditions, the carbonate ions and ammonium ions as main components of the salts are more efficiently decomposed. As a result, the content of the respective ions in the organic phase can be sufficiently reduced to approximately the same content of the respective ions in the dicyanobenzene-absorbing solution in the absorption step. Due to the reduction of the salts, the loss of dicyanobenzene resulting from deterioration can be suppressed.

The apparatus for use in the method for decomposing and separating one or more salts selected from the group consisting of ammonium carbonate, ammonium bicarbonate, and ammonium carbamate in an organic phase may be a column or a tank, and is not particularly limited as long as the organic phase can be set at the above-described pressure and temperature. For example, when the salts are decomposed and separated from the organic phase with use of a column (degassing column) in the present step, carbon dioxide and ammonia formed from decomposition of the salts, water, and an organic solvent are discharged from the top of the column. On the other hand, the organic phase with a part of or the whole of the salts to be decomposed and removed is extracted from the bottom of the column. The water and the organic solvent discharged from the top of the column are collected into a condenser or the like so as to be further separated into the water and the organic solvent. The organic solvent may be returned to the degassing column. When the separation of the collected water and organic solvent is difficult, the water and the organic solvent as such may be returned to the degassing column without separation of the water, so that the water may be separated from the organic solvent and removed in a low-boiling-point compound separation step in the subsequent stage.

The organic phase to be fed to an apparatus for use in the present step such as a degassing column is preferably heated before feed to a temperature approximately equal to the temperature at the bottom of the degassing column.

In the degassing step, the apparatuses for use in the method for decomposing and separating the salts may be placed in series, such that each of the apparatuses decomposes the salts for separation from the organic phase. In that case, the organic phase obtained by the decomposition and separation of a part of the salts with an apparatus in the preceding stage may be fed to an apparatus in the subsequent stage, so that an organic phase with the salts further decomposed and separated can be obtained with the apparatus in the subsequent stage.

The method for producing dicyanobenzene in the present embodiment can remove the salts and water, which are conventionally brought into an apparatus for use in the following low-boiling-point compound separation step, from an organic phase in the degassing step, in advance. Consequently, reduction in the operation load in the low-boiling-point compound separation step, e.g. reduction in the temperature and pressure load required for separating the salts and water from dicyanobenzene, can be achieved.

(5) Low-Boiling-Point Compound Separation Step

In the low-boiling-point compound separation step, the organic phase after the degassing step is distilled to separate low boiling point compounds contained in the organic phase from the organic phase, so that dicyanobenzene is obtained. In the step, a part of or the whole of the low boiling point compounds is separated from the organic phase. Further, in the step, dicyanobenzene is obtained in a liquid state, while the low boiling point compounds are separated in a gas state. Further, the low boiling point compounds include organic solvents. The distillation method in the present step is not particularly limited as long as the low boiling point compounds can be removed from the organic phase (i.e. the low boiling point compounds can be separated from dicyanobenzene). Accordingly, the distillation method may be any of a batch type and a continuous type. For example, when the distillation is performed using a distillation column in the present step, low boiling point compounds including the organic solvent may be discharged from only the top of the column, or from both of the top of the column and a side cut part (condensing part located above a raw material feeding part). Further, the discharged low boiling point compounds may be collected and separated into the organic solvent and other low boiling point compounds as necessary. The low boiling point compounds including the organic solvent or the organic solvent may be then used as an organic solvent for absorbing dicyanobenzene contained in the ammoxidation reaction gas in the absorption step. Further, in order to stabilize the feed flow rate of the organic phase to an apparatus such as a distillation column for use in distillation in the low-boiling-point compound separation step, the organic phase after the degassing step may be once reserved in a tank or the like and then fed to an apparatus for use in the low-boiling-point compound separation step.

The pressure of distillation in the present step is preferably under a reduced pressure, more preferably 1 to 30 kPa at the gas phase side (at the top of column, when a distillation column is used). With a pressure in the range, the deterioration of dicyanobenzene can be more effectively and reliably suppressed. The temperature of distillation is preferably a temperature at which no dicyanobenzene precipitates. For example, when a distillation column is used, a temperature at which no dicyanobenzene precipitates at the condensation part (above the raw material feed part) is preferred. When a distillation column is used, dicyanobenzene in a liquid state (a melt state) is obtained from the bottom of the distillation column.

The feed temperature of the organic phase to an apparatus for use in distillation (e.g. distillation column) may be approximately the same as the temperature of the liquid phase in the immediately preceding step. Further, the temperature of the liquid phase in the apparatus for use in distillation (temperature at the bottom of the column, when a distillation column is used) is preferably a temperature equal to or higher than the melting point of dicyanobenzene and as low as possible, in order to suppress the formation of the group of multimers of dicyanobenzene due to heating. More specifically the temperature of the liquid phase is preferably 150 to 200° C., more preferably 150 to 180° C., furthermore preferably 150 to 170° C., for phthalonitrile as dicyanobenzene. The temperature of the liquid phase is preferably 170 to 220° C., more preferably 170 to 200° C., furthermore preferably 170 to 190° C., for isophthalonitrile as dicyanobenzene. The temperature of the liquid phase is preferably 240 to 290° C., more preferably 240 to 270° C., furthermore preferably 240 to 260° C., for terephthalonitrile as dicyanobenzene. Further, in order to suppress the formation of the group of multimers of dicyanobenzene in the liquid phase (at the bottom of the column, in the case of a distillation column), a shorter residence time of dicyanobenzene in a melt state is preferred. For example, the residence time of dicyanobenzene is preferably 180 minutes or less, more preferably 10 to 120 minutes, furthermore preferably 15 to 60 minutes, particularly preferably 20 to 30 minutes. From the same viewpoint, the volume at the bottom of a column is preferably down-sized as small as possible within a range not causing troubles in operation of a distillation column in designing of a distillation column.

In the low-boiling-point compound separation step, the apparatuses for use in separation of low boiling point compounds from an organic phase by distillation may be disposed in series, so that the low boiling point compounds can be separated from the organic phase by distillation in each of the apparatuses. In that case, the dicyanobenzene-containing organic phase obtained by distillation to separate a part of low boiling point compounds in an apparatus in the preceding stage is fed to an apparatus in the subsequent stage, and a part of or the whole of low boiling point compounds is further separated by distillation in the apparatus in the subsequent stage, so that the dicyanobenzene-containing organic phase can be obtained.

The dicyanobenzene obtained by the producing method in the present embodiment is subjected to a hydrogenation step described below, so that xylylenediamine can be produced. Herein, "xylylenediamine" means ortho-xylylenediamine, meta-xylylenediamine, or para-xylylenediamine, which may be produced by hydrogenating corresponding phthalonitrile (i.e. 1,2-dicyanobenzene), isophthalonitrile (i.e. 1,3-dicyanobenzene), or terephthalonitrile (i.e. 1,4-dicyanobenzene), respectively.

(6) Hydrogenation Step

In the hydrogenation step, dicyanobenzene in a melt state after the low-boiling-point compound separation step is dissolved in a solvent and then hydrogenated in the liquid phase in the presence of a catalyst. Examples of the solvent include liquid ammonia, a mixed solvent of xylylenediamine and liquid ammonia, a mixed solvent of an aromatic hydrocarbon (e.g. xylene, mesitylene and pseudocumene) and liquid ammonia, and a mixed solvent of xylylenediamine, an aromatic hydrocarbon, and liquid ammonia.

The higher the concentration of liquid ammonia in a solvent is, the more the yield of xylylenediamine in a hydrogenation reaction can be increased. Therefore, a high concentration of liquid ammonia in a solvent is preferred. For example, a concentration of 60% by mass or more is preferred and a concentration of 100% by mass is particularly preferred.

The solvent amount in the hydrogenation reaction is preferably 1 to 99 parts by mass, more preferably 3 to 99 parts by mass, furthermore preferably 5 to 99 parts by mass, based on 1 part by mass of dicyanobenzene. With a solvent amount in the range, the energy required for solvent collection can be further reduced, achieving economical advantages, capable of further improving the selectivity of xylylenediamine in the hydrogenation reaction.

The operation for dissolving dicyanobenzene in a melt state into a solvent may be also performed by using a tube-type mixer such as a static mixer. Use of a tube-type mixer, however, may cause clogging in the mixer due to adhesion of precipitated insoluble components. From the viewpoint of preventing the situation, dicyanobenzene is preferably mixed with and dissolved in a solvent in a dissolution tank. When dicyanobenzene in a melt state and a solvent are fed to a dissolution tank, dissolution may be performed without particular agitation. Agitation may be performed as necessary. The pressure and the temperature in the dissolution tank are selected such that the solvent maintains a liquid phase and dicyanobenzene is more easily dissolved in the solvent. From such a viewpoint, more specifically the pressure in the dissolution tank is preferably 0.5 to 15 MPa, more preferably 0.7 to 10 MPa, furthermore preferably 1 to 8 MPa. From the same viewpoint, the solution temperature in the dissolution tank is preferably 3 to 140° C., more preferably 5 to 120° C., furthermore preferably 10 to 100° C.

When insoluble components are formed in the solution, a part of or the whole of the components may be removed by solid-liquid separation prior to feed to the hydrogenation reaction. The solid-liquid separation may be performed by a known method such as filtration, centrifugal separation, and sedimentation separation. Among them, filtration is preferred, and filtration using a sintered metal filter and/or a strainer is particularly simple and suitable.

Hydrogen to be fed to the hydrogenation reaction may contain impurities inert to the reaction, such as methane and nitrogen. However, reduction in impurity concentration in hydrogen for more easily securing a necessary hydrogen partial pressure with a reduced total reaction pressure is more industrially advantageous. Accordingly, the hydrogen concentration is preferably 50 mol % or more.

As a catalyst for the hydrogenation reaction, a known catalyst such as a supported metal catalyst, a non-supported metal catalyst, a Raney catalyst and a noble metal catalyst, may be used. Among these, a catalyst containing nickel and/or cobalt can be suitably used. The amount of catalyst for use is not particularly limited as long as the amount can be employed for known liquid phase hydrogenation of dicyanobenzene.

In the hydrogenation reaction, the type of a catalyst bed may be any of a fixed bed and a slurry bed. Further, in the hydrogenation reaction, any of a batch process and a continuous process may be used. When a continuous flow reaction is performed with a fixed catalyst bed, a circulation process may be employed, in which a part of the hydrogenation reaction liquid obtained from the outlet of the hydrogenation reactor is continuously returned to the hydrogenation reactor. In that case, the circulation process may be employed alone, or the circulation process and a one-pass process may be combined for use as described in Japanese Patent Application Laid-Open No. 2008-31155. When a hydrogenation reaction is performed by a batch process, the hydrogenation reaction time is preferably 0.5 to 8 hours. When a hydrogenation reaction is performed by a continuous process, the liquid hourly space velocity (LHSV) of a reaction raw material is preferably 0.1 to 10 $h^{-1}$.

The pressure and the temperature in a hydrogenation reaction are selected such that the hydrogenation reaction proceeds and the solvent maintains a liquid phase. The temperature of a hydrogenation reaction is preferably 20 to 200° C., more preferably 30 to 150° C., furthermore preferably 40 to 120° C. The hydrogen pressure in a hydrogenation reaction is preferably 1 to 30 MPa, more preferably 2 to 25 MPa, furthermore preferably 3 to 20 MPa.

In order to efficiently produce xylylenediamine in hydrogenation of dicyanobenzene, preferably the progress in the hydrogenation reaction from a nitrile group to an aminomethyl group is accelerated. For that reason, preferably reaction conditions are selected such that the concentrations of dicyanobenzene and cyanobenzylamine are kept at low levels in the liquid to be obtained after the hydrogenation reaction. More specifically, the amount of cyanobenzylamine based on 100% by mass of xylylenediamine in the liquid to be obtained after the hydrogenation reaction is kept preferably 5.0% by mass or less, more preferably 1.0% by mass or less, furthermore preferably 0.2% by mass or less. The conversion of dicyanobenzene is preferably 99.50% or more, more preferably 99.90% or more, furthermore preferably 99.95% or more. In the combinations of each of the reaction conditions (e.g. solvent, catalyst, raw material, hydrogen pressure, and reaction method), the temperature or the time is properly selected, so that the progress of the hydrogenation reaction can be maintained as described above.

The xylylenediamine formed by the hydrogenation reaction may be refined by a known method such as distillation. In the case of producing xylylenediamine having higher purity, preferably cyanobenzylamine contained together with xylylenediamine in the liquid after the hydrogenation reaction is removed. However, since the difference in the boiling point between cyanobenzylamine and corresponding xylylenediamine is small in general, the separation by normal distillation is difficult. Accordingly, cyanobenzylamine may be removed from the liquid before distillation of the liquid after hydrogenation reaction by a method other than distillation. Examples of the method for removing cyanobenzylamine include, but not particularly limited to: a method involving converting cyanobenzylamine into cyanobenzamide by hydration reaction, which is relatively easily separated by distillation; and a method involving reducing the amount of cyanobenzylamine by catalytic hydrogenation of cyanobenzylamine in the presence of a catalyst after removal of liquid ammonia as a hydrogenation solvent as described in Japanese Patent Application Laid-Open No. 2007-332135.

(Apparatus for Producing Dicyanobenzene)

A producing apparatus for use in the producing method of dicyanobenzene of the present embodiment includes: (1) absorption means for contacting a xylene-ammoxidation reaction gas containing dicyanobenzene obtained by ammoxidation of xylene with an organic solvent so as to obtain a dicyanobenzene-absorbing solution containing the organic solvent in which the dicyanobenzene is dissolved; (2) extraction means of contacting the dicyanobenzene-absorbing solution with a basic aqueous solution containing one or more salts selected from the group consisting of ammonium carbonate, ammonium bicarbonate, and ammonium carbamate so as to extract a water-soluble salt formed by neutralization reaction between a carboxylic acid in the dicyanobenzene-absorbing solution and a base in the basic aqueous solution into an aqueous phase; (3) liquid-liquid separation means of separating the mixture of the dicyanobenzene-absorbing solution and the basic aqueous solution sent from the extraction means into an organic phase and an aqueous phase; (4) degassing means of decomposing one or more salts selected from the group consisting of ammonium carbonate, ammonium bicarbonate and ammonium carbamate contained in the organic phase sent from the liquid-liquid separation means, so as to separate the one or more salts from the organic phase; and (5) low-boiling-point compound separation means of distilling the organic phase sent from the degassing means to separate the components contained in the organic phase and having a boiling point lower than that of dicyanobenzene, from the organic phase so as to obtain dicyanobenzene.

Figure 1:
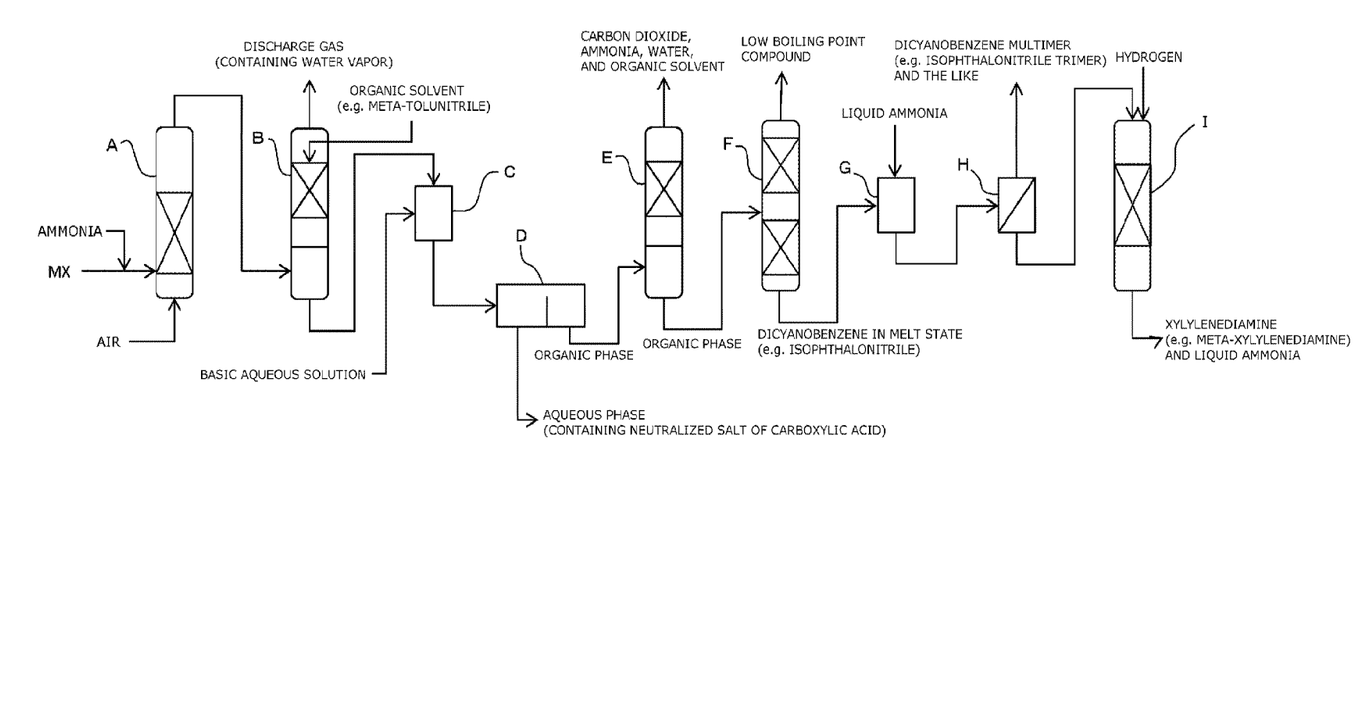
FIG. 1 is a schematic view of a producing apparatus for use in the method for producing dicyanobenzene of the present invention.

FIG. 1 is a schematic view of a producing apparatus for use in the method for producing dicyanobenzene of the present embodiment, more specifically a process flow sheet of an apparatus for producing isophthalonitrile by ammoxidation reaction. The producing apparatus includes an ammoxidation reactor A as means for proceeding the ammoxidation reaction, an absorption column B as the absorbing means, a mixing tank C as the extraction means and as a part of the liquid-liquid separation means, a liquid-liquid separation tank D as the liquid-liquid separation means, a degassing column E as the degassing means, a low-boiling-point compound separation column F as the low-boiling-point compound separation means, a dissolution tank G as dissolution means for dissolving dicyanobenzene in a solvent, a filtration device H as means for filtering insoluble components in the solution sent from the dissolution tank G, and a hydrogenation reactor I as means for proceeding the hydrogenation reaction of dicyanobenzene using, as raw material, the liquid sent from the filtration device H.

The ammoxidation reactor A and the hydrogenation reactor I are charged with catalysts for use in the respective reactions. The ammoxidation reactor A, the absorption column B, the mixing tank C, the liquid-liquid separation tank D, the degassing column E, the low-boiling-point compound separation column F, the dissolution tank G, the filtration device H, and the hydrogenation reactor I each are connected to piping for receiving a gas or a liquid sent from an apparatus in the preceding stage, and to piping for sending a gas or a liquid subjected to a predetermined treatment at the apparatus to an apparatus in the subsequent stage. Further, the ammoxidation reactor A, the absorption column B, the mixing tank C, the liquid-liquid separation tank D, the degassing column E, the low-boiling-point compound separation column F, the dissolution tank G, the filtration device H, and the hydrogenation reactor I each may be provided with heating means such as a heat exchanger as necessary. Each piping may be provided with valves for controlling the pressure of the respective apparatuses, or for controlling the flow rate of the gas or liquid to be received by the respective apparatuses or to be sent from the respective apparatuses. Further, although the mixing tank C and the liquid-liquid separation tank D are different tanks in FIG. 1, one tank may be used as both of the mixing tank C and the liquid-liquid separation tank D.

Since the type, the operation conditions and the like of each of the apparatuses are the same as those described in the "(Method for producing dicyanobenzene)", the explanation is omitted here.

EXAMPLES

With reference to the following Examples, the present invention will be more specifically described below. The present invention, however, is not limited to these Examples.

In analysis of the organic impurities contained in dicyanobenzene (e.g. cyanobenzamide and cyanobenzoic acid), liquid chromatography was used. In analysis of the dicyanobenzene-absorbing solution, dicyanobenzene, or the liquid after hydrogenation reaction (a mixture of the unreacted residues of materials fed to the hydrogenation reaction and the products of the hydrogenation reaction), gas chromatography was used. Further, with regard to an organic phase, the water content was analyzed by a trace moisture meter, the carbonate ion concentration was analyzed by titration, and the ammonium ion concentration was analyzed by an electrophoresis apparatus. The salt concentration was converted in terms of carbonate ion concentration.

(1) Liquid Chromatography Analysis

In liquid chromatography analysis, a high pressure gradient LC system with a UV-VIS detector manufactured by Shimadzu Corporation, having an LC column CAPCELL PAK C18 (trade name) manufactured by Shiseido Co., Ltd., was used. A mixture of acetonitrile (special grade, produced by Wako Pure Chemical Industries, Ltd.) and 0.5% by mass phosphoric acid aqueous solution was used as a solvent and a moving phase. The organic impurities contained in dicyanobenzene were analyzed under conditions of a column oven temperature of 35° C., and a flow rate of the moving phase of 1.0 mL/min.

(2) Gas Chromatography Analysis

In gas chromatography analysis, a GC analyzer 6890-TYPE manufactured by Agilent Technologies, having a GC column DB-1 manufactured by J & W Scientific was used. The temperature was adjusted to 230° C. at the sample injection port, and 295° C. at the detector. The temperature of the column oven was kept at 100° C. for 10 minutes and then elevated to 280° C. at a temperature increase rate of 5° C./min. The GC measurement samples of the dicyanobenzene-absorbing solution and dicyanobenzene were prepared by adding 0.1 g of diphenylmethane (special grade, produced by Wako Pure Chemical Industries, Ltd.) as internal standard to 0.1 g of the measurement specimen, and dissolving the mixture in 10 g of acetone solvent (special grade, produced by Wako Pure Chemical Industries, Ltd.). The GC measurement sample of the product liquid of the hydrogenation reaction was prepared by adding 0.1 g of diphenylmethane (special grade, produced by Wako Pure Chemical Industries, Ltd.) as internal standard to 0.2 g of crude meta-xylylenediamine after removal of ammonia from the product liquid of the hydrogenation reaction, and dissolving the mixture in 10 g of a methanol solvent or a dioxane solvent (both: special grade, produced by Wako Pure Chemical Industries, Ltd.).

(3) Analysis of Water Content in Organic Phase

A pressure-resistant container (50 mL, made of SUS 304) under a nitrogen atmosphere was charged with 40 g of meta-tolunitrile, into which the organic phase after liquid-liquid separation or after degassing was sampled in a sealed system so as to prepare a sample liquid. After the container temperature is lowered to room temperature, the sample liquid was taken out from the container and subjected to quantitative determination of the water content with a trace moisture meter CA-100 TYPE manufactured by Mitsubishi Chemical Corporation.

(4) Analysis of Salts in Organic Phase (4-1) Analysis of Carbonate Ion Concentration A pressure-resistant container (50 mL, made of SUS 304) under a nitrogen atmosphere was charged with 8 g of 10% by mass barium chloride aqueous solution and 35 g of meta-tolunitrile, into which the organic phase after liquid-liquid separation or after degassing was sampled in a sealed system. The insoluble content formed in sampling was collected by suction filtration. The insoluble content was then placed in a beaker, into which 10 mL of 0.1 N hydrochloric acid (produced by Wako Pure Chemical Industries, Ltd.) was added, and the insoluble content was dissolved by heating. After cooling, titration was performed with 0.1 N sodium hydroxide aqueous solution (produced by Wako Pure Chemical Industries, Ltd.) to determine the quantity of carbonate ion $CO_3^{2-}$.

(4-2) Analysis of Ammonium Ion Concentration

A pressure-resistant container (50 mL, made of SUS 304) under a nitrogen atmosphere was charged with 8 g of 0.1 N dilute sulfuric acid and 35 g of meta-tolunitrile, into which the organic phase after liquid-liquid separation or after degassing was sampled in a sealed system. After the organic phase was sufficiently dissolved in the pressure-resistant container, the water phase part of the sample collected from the pressure-resistant container was fractionated and analyzed by an electrophoresis apparatus manufactured by Otsuka Electronics Co., Ltd., so as to determine the quantity of ammonium ion $NH_4^+$.

Example 1

[Ammoxidation Step]

To 229 g of vanadium pentoxide (special grade, produced by Wako Pure Chemical Industries, Ltd.), 500 mL of water (distilled water) was added. The mixture was heated to 80 to 90° C., and 477 g of oxalic acid (special grade, produced by Wako Pure Chemical Industries, Ltd.) was added thereto to be dissolved while agitating, so that a solution of vanadium oxalate was obtained. Further, to 963 g of oxalic acid, 400 mL of water was added. The mixture was heated to 50 to 60° C., and a solution of 252 g of chromic anhydride (special grade, produced by Wako Pure Chemical Industries, Ltd.) in 200 mL of water was added thereto to be dissolved while agitating well, so that a solution of chromium oxalate was obtained. The solution of vanadium oxalate obtained was mixed with the solution of chromium oxalate at 50 to 60° C., so that a vanadium-chromium solution was obtained. To the vanadium-chromium solution, 41.1 g of phosphomolybdic acid ($H_3(PMo_{12}O_{40}) \cdot 20H_2O$, produced by Nippon Inorganic Colour & Chemical Co., Ltd.) dissolved in 100 mL of water was added, to which 4.0 g of potassium acetate (special grade, produced by Wako Pure Chemical Industries, Ltd.) dissolved in 100 mL of water was further added, and subsequently 2500 g of 20% by mass aqueous silica sol (containing 0.02% by mass Na$_2$O) was added thereto to obtain a slurry solution. To the slurry solution, 78 g of boric acid was added and sufficiently mixed. The mixture was heated and condensed until the liquid amount reached about 3800 g, so that a catalyst solution was obtained. The catalyst solution was spray-dried under air flow with a spray dryer with an inlet temperature kept at 250° C. and an outlet temperature kept at 130° C., so that catalyst precursor particles were obtained. The catalyst precursor particles were dried under air atmosphere at 130° C. for 12 hours with a dryer, then fired under air flow at 400° C. for 0.5 hours with a firing apparatus, and further fired under air flow at 550° C. for 8 hours, so that a catalyst was obtained. The catalyst had an atomic ratio V:Cr:B:Mo:P:Na:K of 1:1:0.5:0.086:0.007: 0.009:0.020, and a catalyst concentration of 50% by mass based on the total catalyst mass.

Using the same producing apparatuses as those illustrated in FIG. 1, dicyanobenzene was produced as follows. An ammoxidation reactor A was filled with 6 L of the catalyst prepared as described above, and a fluidized bed was employed as the catalyst bed. a mixed gas obtained by mixing air as an oxygen supply source, meta-xylene (hereinafter abbreviated as "MX", produced by Mitsubishi Gas Chemical Company, Inc.) and ammonia (produced by Mitsubishi Gas Chemical Company, Inc.) was preheated to 350° C. and fed to the reactor A. The feed conditions was as follows: an amount of MX fed of 350 g/h, a molar ratio ammonia/MX of 10, a molar ratio oxygen/MX of 5.4, a gas hourly space velocity (GHSV) of 630 h$^{-1}$. The reaction temperature was 420° C., and the reaction pressure was 0.2 MPa.

(1) Absorption Step

The ammoxidation reaction gas extracted from the top of the ammoxidation reactor A was introduced to an isophthalonitrile absorption column B, so that isophthalonitrile in the ammoxidation reaction gas was absorbed in the meta-tolunitrile (produced by Mitsubishi Gas Chemical Company, Inc.) solvent. The isophthalonitrile absorption column B made of SUS 304 was connected to the piping for discharging at the top, having a body part with an inner diameter ϕ of 100 mm and a height of 800 mm, of which the lower portion with a length of 450 mm included a double pipe structure capable of steam heating, and the bottom was provided with an injection inlet for feed of the ammoxidation reaction gas. 2 kg of meta-tolunitrile was introduced into the absorption column B and kept in the column at 140° C. The ammoxidation reaction gas was fed from the injection inlet at a flow rate of 353 g/hr, and the ammoxidation reaction gas was absorbed by the meta-tolunitrile for 2 hours. The piping for discharging was provided with a pressure control valve, so that the pressure in the absorption column B was controlled at a constant pressure. The contact time between the ammoxidation reaction gas and the meta-tolunitrile was 1 to 2 seconds. At the completion of absorption, the dicyanobenzene (isophthalonitrile) absorbing solution had a water content of 0.16% by mass, a carbonate ion concentration of 108 ppm by mass, and an ammonium ion concentration of 1203 ppm by mass. The composition of the isophthalonitrile absorbing solution included 24.98% by mass of isophthalonitrile, 73.89% by mass of meta-tolunitrile, and 0.467% by mass of 3-cyanobenzamide, and 0.156% by mass of 3-cyanobenzoic acid (2) Extraction Step A mixing tank C was fully filled with 235 g of the isophthalonitrile absorbing solution, and the liquid temperature was adjusted to 100° C. As the mixing tank C, an autoclave (made of SUS 304; capacity: 250 mL; having a back pressure valve set to 0.5 MPaG at the top, and a nozzle at the bottom) provided with a heater and an agitator was employed. The isophthalonitrile absorbing solution was heated to a prescribed temperature while agitating, and then the agitation was temporarily stopped. Subsequently 39.6 g of a basic aqueous solution prepared by dissolving 1.58 g of 25% ammonia water (special grade, produced by Wako Pure Chemical Industries, Ltd.) and 3.96 g of ammonium carbonate (special grade, produced by Wako Pure Chemical Industries, Ltd.) dissolved in 34.06 g of pure water was fed at a rate of 5 g/min from the nozzle at the bottom of the mixing tank C, and the isophthalonitrile absorbing solution overflowing from the back pressure valve at the top was extracted to keep the pressure in the mixing tank C at 0.5 MPaG. In the mixing tank, 198 g of the isophthalonitrile absorbing solution remained. Subsequently the agitation was restarted and the liquid temperature was adjusted to 100° C. The agitation operation was maintained at 1000 rpm for 10 minutes.

(3) Liquid-Liquid Separation Step

The agitation in the mixing tank C was stopped, and the mixture of the isophthalonitrile absorbing solution and the basic aqueous solution was left at rest for 10 minutes while keeping the liquid temperature at 100° C., so that the mixture was separated into an organic phase (upper layer) and an aqueous phase (lower layer). In other words, the mixing tank C was used also as a liquid-liquid separation tank D. Subsequently a basic aqueous solution having the same composition as that prepared in the extraction step was fed from the nozzle at the bottom of the mixing tank C at a rate of 2 g/min, and 120 g of the organic phase after liquid-liquid separation was continuously extracted from the back pressure valve at the top. The extracted organic phase had a water content of 3.04% by mass, a carbonate ion concentration of 2223 ppm by mass, and an ammonium ion concentration of 1312 ppm by mass, and an ammonium carbonate salt concentration of 3556 ppm by mass. The composition of the organic phase included 24.26% by mass of isophthalonitrile, 71.73% by mass of meta-tolunitrile, 0.454% by mass of 3-cyanobenzamide, and 0.011% by mass of 3-cyanobenzoic acid.

(4) Degassing Step

The organic phase extracted from the liquid-liquid separation tank D was directly fed to a continuous type degassing column E. The organic phase to be fed had a temperature of 140° C., and a feed rate of 2 g/min. The temperature at the bottom of the column was controlled to the same temperature as the feed temperature, and the pressure at the top of the column was controlled to 101.3 kPa. Carbon dioxide and ammonia generated by decomposition of the salts were discharged from the top of the degassing column E. Further, water and the organic solvent discharged together with carbon dioxide and ammonia from the top of the column were collected, and all of the water and the organic solvent were returned to the degassing column E without separation. The organic phase obtained from the bottom of the column had a water content of 3.01% by mass, a carbonate ion concentration of 51 ppm by mass, an ammonium ion concentration of 151 ppm by mass, and an ammonium carbonate salt concentration of 81 ppm by mass. The composition of the organic phase included 24.35% by mass of isophthalonitrile, 72.00% by mass of meta-tolunitrile, 0.455% by mass of 3-cyanobenzamide, and 0.011% by mass of 3-cyanobenzoic acid.

(5) Low-Boiling-Point Compound Separation Step

The organic phase extracted from the bottom of the degassing column E was directly fed to the middle stage of a low-boiling-point compound separation column F as a continuous distillation column. The temperature of the organic phase to be fed was controlled to the same as the temperature at the bottom of the column in the preceding step, and the feed rate was controlled at 2 g/min. The conditions of the low-boiling-point compound separation column F included a pressure at the top of the column of 5 kPa, a temperature at the top of the column of 120° C., a temperature at the bottom of the column of 180° C., and a residence time at the bottom of the column of 20 minutes. Meta-tolunitrile and other low boiling point compounds were removed from the top of the low-boiling-point compound separation column F, while an organic phase mainly containing isophthalonitrile in a melt state was extracted from the bottom of the column. The composition of the organic phase obtained from the bottom of the column included 97.39% by mass of isophthalonitrile, 0.10% by mass of meta-tolunitrile, 1.821% by mass of 3-cyanobenzamide, and 0.043% by mass of 3-cyanobenzoic acid.

Example 2

(6) Hydrogenation Step

In a dissolution tank G (made of SUS 304), 1 part by mass of the organic phase mainly containing isophthalonitrile in a melt state obtained in Example 1 was dissolved in 9 parts by mass of liquid ammonia under conditions at 2 MPa and 25° C. Subsequently a solution containing insoluble components was extracted from the bottom of the dissolution tank G, and subjected to filtration by liquid transfer with utilization of pressure difference, using a sintered metal filter (pore size: 40 μm, made of stainless steel) as filtration device H, so that a hydrogenation raw material liquid containing isophthalonitrile was obtained.

A vertical tubular type hydrogenation reactor I (made of SUS 304, inner diameter φ: 13 mm) was filled with 25 g of crushed particles with a uniform size (12 to 22 mesh/JIS standard) of commercially available supported nickel/diatomaceous earth catalyst with a nickel content of 50% by mass (cylindrical shape, diameter φ: 3 mm, height: 3 mm), and reduced at 200° C. under hydrogen gas flow for activation. After cooling, hydrogen gas was injected into the reactor I to keep a constant pressure of 8 MPa. The temperature of the catalyst layer was maintained at 80° C. by heating from outside. While hydrogen gas was fed and circulated at a rate of 18 NL/hr from the top of the reactor I, the hydrogenation raw material liquid was continuously fed from the top of the reactor at the rate of 25.0 g/hr. The hydrogenation raw material liquid and hydrogen passed through the catalyst layer and the hydrogenation reaction liquid was obtained from the bottom of the reactor. Ammonia was then removed from the hydrogenation reaction liquid, so that crude meta-xylylenediamine was obtained. The composition of the crude meta-xylylenediamine obtained included 91.16% by mass of meta-xylylenediamine and 0.10% by mass of 3-methylbenzylamine, and no isophthalonitrile was detected. The remaining components included oligomers of meta-xylylenediamine and high boiling point polymers not detectable by gas chromatography.

Example 3

Dicyanobenzene was produced using the same conditions and procedures as in Example 1, except that in the degassing step (4), water and the organic solvent discharged from the top of the degassing column E were separated into water and the organic solvent and the organic solvent alone was returned to the degassing step.

In the degassing step, the organic phase obtained from the bottom of the degassing column E had a water content of 0.99% by mass, a carbonate ion concentration of 51 ppm by mass, an ammonium ion concentration of 151 ppm by mass, and an ammonium carbonate salt concentration of 81 ppm by mass. The composition of the organic phase included 24.86% by mass of isophthalonitrile, 73.50% by mass of meta-tolunitrile, 0.465% by mass of 3-cyanobenzamide, and 0.011% by mass of 3-cyanobenzoic acid.

In the low-boiling-point compound separation step, the composition of the organic phase obtained from the bottom of the low-boiling-point compound separation column F included 97.42% by mass of isophthalonitrile, 0.10% by mass of meta-tolunitrile, 1.844% by mass of 3-cyanobenzamide, and 0.039% by mass of 3-cyanobenzoic acid. In comparison with Example 1, the concentration of isophthalonitrile was approximately the same.

Example 4

The organic phase mainly containing the isophthalonitrile in a melt state obtained in Example 3 was hydrogenated by the same method as in the hydrogenation step in Example 2. The composition of the crude meta-xylylenediamine obtained included 91.18% by mass of meta-xylylenediamine and 0.10% by mass of 3-methylbenzylamine, and no isophthalonitrile was detected. The remaining components included oligomers of meta-xylylenediamine and high boiling point polymers not detectable by gas chromatography. In comparison with Example 2, the concentration of meta-xylylenediamine was approximately the same.

Example 5

Dicyanobenzene was produced using the same conditions and procedures as in Example 1, except that the temperature of the organic phase obtained in the liquid-liquid separation step (3) and fed to the degassing column E, and the temperature at the bottom of the degassing column E were controlled to 180° C.

In the degassing step, the organic phase obtained from the bottom of the degassing column E had a water content of 2.98% by mass, a carbonate ion concentration of 25 ppm by mass, an ammonium ion concentration of 75 ppm by mass, and an ammonium carbonate salt concentration of 41 ppm by mass. The composition of the organic phase included 24.36% by mass of isophthalonitrile, 72.03% by mass of meta-tolunitrile, 0.455% by mass of 3-cyanobenzamide, and 0.011% by mass of 3-cyanobenzoic acid.

In the low-boiling-point compound separation step, the composition of the organic phase obtained from the bottom of the low-boiling-point compound separation column F included 97.30% by mass of isophthalonitrile, 0.10% by mass of meta-tolunitrile, 1.920% by mass of 3-cyanobenzamide, and 0.040% by mass of 3-cyanobenzoic acid. In comparison with Example 1, the concentration of isophthalonitrile decreased slightly.

Example 6

The organic phase mainly containing the isophthalonitrile in a melt state obtained in Example 5 was hydrogenated by the same method as in the hydrogenation step in Example 2.

The composition of the crude meta-xylylenediamine obtained included 91.07% by mass of meta-xylylenediamine and 0.10% by mass of 3-methylbenzylamine, and no isophthalonitrile was detected. The remaining components included oligomers of meta-xylylenediamine and high boiling point polymers not detectable by gas chromatography. In comparison with Example 2, the concentration of meta-xylylenediamine decreased slightly.

Example 7

Dicyanobenzene was produced using the same conditions and procedures as in Example 1, except that the temperature of the organic phase obtained in the liquid-liquid separation step (3) and fed to the degassing column E, and the temperature at the bottom of the degassing column E were controlled to 180° C., and the water and organic solvent discharged from the top of the degassing column E in the degassing step (4) were separated into water and the organic solvent and the organic solvent alone was returned to the degassing step.

In the degassing step, the organic phase obtained from the bottom of the degassing column E had a water content of 0.26% by mass, a carbonate ion concentration of 25 ppm by mass, an ammonium ion concentration of 75 ppm by mass, and an ammonium carbonate salt concentration of 41 ppm by mass. The composition of the organic phase included 25.04% by mass of isophthalonitrile, 74.05% by mass of meta-tolunitrile, 0.468% by mass of 3-cyanobenzamide, and 0.011% by mass of 3-cyanobenzoic acid.

In the low-boiling-point compound separation step, the composition of the organic phase obtained from the bottom of the low-boiling-point compound separation column F included 97.43% by mass of isophthalonitrile, 0.10% by mass of meta-tolunitrile, 1.839% by mass of 3-cyanobenzamide, and 0.038% by mass of 3-cyanobenzoic acid. In comparison with Example 1, the concentration of isophthalonitrile was approximately the same.

Example 8

The organic phase mainly containing the isophthalonitrile in a melt state obtained in Example 7 was hydrogenated by the same method as in the hydrogenation step in Example 2. The composition of the crude meta-xylylenediamine obtained included 91.19% by mass of meta-xylylenediamine and 0.10% by mass of 3-methylbenzylamine, and no isophthalonitrile was detected. The remaining components included oligomers of meta-xylylenediamine and high boiling point polymers not detectable by gas chromatography. In comparison with Example 2, the concentration of meta-xylylenediamine was approximately the same.

Comparative Example 1

Dicyanobenzene was produced using the same conditions and procedures as in Example 1, except that the degassing step (4) was omitted and the organic phase obtained in the liquid-liquid separation step (3) was directly fed to the low-boiling-point compound separation column F. The temperature of the organic phase to be fed to the low-boiling-point compound separation column F was controlled at 140° C., and the feed rate was controlled at 2 g/min, which were the same conditions as in Example 1.

In the low-boiling-point compound separation step, the composition of the organic phase mainly containing isophthalonitrile in a melt state obtained from the bottom of the low-boiling-point compound separation column F included 97.20% by mass of isophthalonitrile, 0.10% by mass of meta-tolunitrile, 2.017% by mass of 3-cyanobenzamide, and 0.043% by mass of 3-cyanobenzoic acid. In comparison with Example 1, the concentration of isophthalonitrile decreased by 0.19% by mass, and the deterioration of isophthalonitrile was observed. In comparison with Example 1, 3-cyanobenzamide increased.

The composition of the crude meta-xylylenediamine obtained through the hydrogenation step in the same way as in Example 2 included 90.98% by mass of meta-xylylenediamine and 0.10% by mass of 3-methylbenzylamine, and no isophthalonitrile was detected. The remaining components included oligomers of meta-xylylenediamine and high boiling point polymers not detectable by gas chromatography. In comparison with Example 2, the concentration of meta-xylylenediamine decreased by 0.18% by mass.

Comparative Example 2

Dicyanobenzene was produced using the same conditions and procedures as in Comparative Example 1, except that the temperature of the organic phase obtained in the liquid-liquid separation step (3) and fed to the low-boiling-point compound separation column F was controlled at 180° C.

In the low-boiling-point compound separation step, the composition of the organic phase mainly containing isophthalonitrile in a melt state obtained from the bottom of the low-boiling-point compound separation column F included 96.97% by mass of isophthalonitrile, 0.10% by mass of meta-tolunitrile, 2.249% by mass of 3-cyanobenzamide, and 0.040% by mass of 3-cyanobenzoic acid. In comparison with Example 1, the concentration of isophthalonitrile decreased by 0.42% by mass, and the deterioration of isophthalonitrile was observed. In comparison with Example 1, 3-cyanobenzamide increased.

The composition of the crude meta-xylylenediamine obtained through the hydrogenation step in the same way as in Example 2 included 90.78% by mass of meta-xylylenediamine and 0.10% by mass of 3-methylbenzylamine, and no isophthalonitrile was detected. The remaining components included oligomers of meta-xylylenediamine and high boiling point polymers not detectable by gas chromatography. In comparison with Example 2, the concentration of meta-xylylenediamine decreased by 0.38% by mass.

Comparative Example 3

Dicyanobenzene was produced using the same conditions and procedures as in Example 1, except that the pressure at the top of the column was changed to 311.3 kPa in the degassing step (4).

In the degassing step, the organic phase obtained from the bottom of the degassing column E had a water content of 3.01% by mass, a carbonate ion concentration of 1673 ppm by mass, an ammonium ion concentration of 874 ppm by mass, and an ammonium carbonate salt concentration of 2677 ppm by mass. The composition of the organic phase included 24.29% by mass of isophthalonitrile, 71.83% by mass of meta-tolunitrile, 0.490% by mass of 3-cyanobenzamide, and 0.011% by mass of 3-cyanobenzoic acid. In comparison with Example 1, the concentration of ammonium carbonate salt increased.

In the low-boiling-point compound separation step, the composition of the organic phase obtained from the bottom of the low-boiling-point compound separation column F included 97.26% by mass of isophthalonitrile, 0.10% by mass of meta-tolunitrile, 1.960% by mass of 3-cyanobenzamide, and 0.043% by mass of 3-cyanobenzoic acid. In comparison with Example 1, the concentration of isophthalonitrile decreased by 0.13% by mass, and the deterioration of isophthalonitrile was observed. In comparison with Example 1, 3-cyanobenzamide increased.

The composition of the crude meta-xylylenediamine obtained through the hydrogenation step in the same way as in Example 2 included 91.03% by mass of meta-xylylenediamine and 0.10% by mass of 3-methylbenzylamine, and no isophthalonitrile was detected. The remaining components included oligomers of meta-xylylenediamine and high boiling point polymers not detectable by gas chromatography. In comparison with Example 2, the concentration of meta-xylylenediamine decreased by 0.13% by mass.

This application is based on Japanese Patent Application filed on Mar. 10, 2014 (Japanese Patent Application No. 2014-046426), the content of which is incorporated by reference herein.

INDUSTRIAL APPLICABILITY

Dicyanobenzene is effective as an agricultural chemical and a functional material. Dicyanobenzene is a useful compound as a raw material of agricultural chemicals and an intermediate raw material of polyamide resins and curing agents, in particular. Further, xylylenediamine is a useful compound in various industrial fields such as resin curing agents, nylon, polyurethane, rubber chemicals, paper processing chemicals, and fiber treatment agents.

REFERENCE SIGNS LIST

A: Ammoxidation reactor, B: Isophthalonitrile absorption column, C: Mixing tank, D: Liquid-liquid separation tank, E: Degassing column, F: Low-boiling-point compound separation column, G: Dissolution tank, H: Filtration device, I: Hydrogenation reactor

The invention claimed is:
1. A method for producing dicyanobenzene comprising:
   (1) an absorption step of contacting a xylene-ammoxidation reaction gas comprising dicyanobenzene obtained by ammoxidation of xylene with an organic solvent so as to obtain a dicyanobenzene-absorbing solution comprising the organic solvent in which the dicyanobenzene is dissolved;
   (2) an extraction step of contacting the dicyanobenzene-absorbing solution with a basic aqueous solution comprising one or more salts selected from the group consisting of ammonium carbonate, ammonium bicarbonate, and ammonium carbamate so as to extract a water-soluble salt formed by neutralization reaction between carboxylic acid in the dicyanobenzene-absorbing solution and a base in the basic aqueous solution into an aqueous phase;
   (3) a liquid-liquid separation step of separating a mixture of the dicyanobenzene-absorbing solution and the basic aqueous solution after the extraction step into an organic phase and an aqueous phase;
   (4) a degassing step of decomposing one or more salts selected from the group consisting of ammonium carbonate, ammonium bicarbonate, and ammonium carbamate contained in the organic phase after the liquid-liquid separation step so as to separate the one or more salts from the organic phase; and
   (5) a low-boiling-point compound separation step of distilling the organic phase after the degassing step to separate components contained in the organic phase and having a boiling point lower than that of the dicyanobenzene, from the organic phase so as to obtain the dicyanobenzene.

2. The method according to claim 1, wherein a pressure of a gas phase in the degassing step is 101.3 kPa or less.

3. The method according to claim 1, wherein a temperature of a liquid phase in the degassing step is 70 to 180° C.

4. The method according to claim 1, wherein the base in the extraction step is ammonia in an amount in a number of moles 1 to 50 times the total number of moles of the carboxylic acid contained in the dicyanobenzene-absorbing solution.

5. The method according to claim 1, wherein the basic aqueous solution is contacted with the dicyanobenzene-absorbing solution under a temperature condition of 140° C. or lower in the extraction step.

6. The method according to claim 1, wherein the xylene is meta-xylene and the dicyanobenzene is isophthalonitrile.

7. The method according to claim 1, wherein a catalyst for use in the ammoxidation reaction is a catalyst which contains vanadium and/or chromium.

8. The method according to claim 1, wherein the organic solvent which absorbs the dicyanobenzene in the absorption step is one or more organic solvents selected from the group consisting of an alkylbenzene, a heterocyclic compound, an aromatic nitrile compound and a heterocyclic nitrile compound.

9. A method for producing xylylenediamine from the dicyanobenzene obtained by the producing method according to claim 1, comprising a hydrogenation step of dissolving the dicyanobenzene in a solvent and subsequently hydrogenating the dicyanobenzene in a liquid phase in the presence of a catalyst.

10. An apparatus for producing dicyanobenzene comprising:
   (1) absorption means for contacting a xylene-ammoxidation reaction gas comprising dicyanobenzene obtained by ammoxidation of xylene with an organic solvent so as to obtain a dicyanobenzene-absorbing solution comprising the organic solvent in which the dicyanobenzene is dissolved;
   (2) extraction means for contacting the dicyanobenzene-absorbing solution with a basic aqueous solution comprising one or more salts selected from the group consisting of ammonium carbonate, ammonium bicarbonate, and ammonium carbamate so as to extract a water-soluble salt formed by neutralization reaction between carboxylic acid in the dicyanobenzene-absorbing solution and a base in the basic aqueous solution into an aqueous phase;
   (3) liquid-liquid separation means for separating a mixture of the dicyanobenzene-absorbing solution and the basic aqueous solution sent from the extraction means into an organic phase and an aqueous phase;
   (4) degassing means for decomposing one or more salts selected from the group consisting of ammonium carbonate, ammonium bicarbonate, and ammonium carbamate contained in the organic phase sent from the liquid-liquid separation means, so as to separate the one or more salts from the organic phase; and
   (5) low-boiling-point compound separation means for distilling the organic phase sent from the degassing means to separate components contained in the organic phase and having a boiling point lower than that of the dicyanobenzene, from the organic phase so as to obtain the dicyanobenzene.

11. The method according to claim 2, wherein a temperature of a liquid phase in the degassing step is 70 to 180° C.

12. The method according to claim 2, wherein the base in the extraction step is ammonia in an amount in a number of moles 1 to 50 times the total number of moles of the carboxylic acid contained in the dicyanobenzene-absorbing solution.

13. The method according to claim 2, wherein the basic aqueous solution is contacted with the dicyanobenzene-absorbing solution under a temperature condition of 140° C. or lower in the extraction step.

14. The method according to claim 2, wherein the xylene is meta-xylene and the dicyanobenzene is isophthalonitrile.

15. The method according to claim 2, wherein a catalyst for use in the ammoxidation reaction is a catalyst which contains vanadium and/or chromium.

16. The method according to claim 2, wherein the organic solvent which absorbs the dicyanobenzene in the absorption step is one or more organic solvents selected from the group consisting of an alkylbenzene, a heterocyclic compound, an aromatic nitrile compound and a heterocyclic nitrile compound.

17. A method for producing xylylenediamine from the dicyanobenzene obtained by the producing method according to claim 2, comprising a hydrogenation step of dissolving the dicyanobenzene in a solvent and subsequently hydrogenating the dicyanobenzene in a liquid phase in the presence of a catalyst.

18. The method according to claim 3, wherein the base in the extraction step is ammonia in an amount in a number of moles 1 to 50 times the total number of moles of the carboxylic acid contained in the dicyanobenzene-absorbing solution.

19. The method according to claim 3, wherein the basic aqueous solution is contacted with the dicyanobenzene-absorbing solution under a temperature condition of 140° C. or lower in the extraction step.

20. The method according to claim 3, wherein the xylene is meta-xylene and the dicyanobenzene is isophthalonitrile.

\* \* \* \* \*